US00PP26845P2

(12) United States Plant Patent
Nishikawa

(10) Patent No.: US PP26,845 P2
(45) Date of Patent: Jun. 21, 2016

(54) ***CALENDULA* PLANT NAMED '20123-29D'**

(50) Latin Name: *Calendula officinalis*
Varietal Denomination: 20123-29D

(71) Applicant: Koichiro Nishikawa, Katuta-Gun (JP)

(72) Inventor: Koichiro Nishikawa, Katuta-Gun (JP)

( * ) Notice: Subject to any disclaimer, the term of this patent is extended or adjusted under 35 U.S.C. 154(b) by 110 days.

(21) Appl. No.: 14/121,630

(22) Filed: Sep. 29, 2014

(51) Int. Cl.
*A01H 5/02* (2006.01)

(52) U.S. Cl.
USPC ..... Plt./263.1

(58) Field of Classification Search
USPC ..... Plt./263.1
See application file for complete search history.

*Primary Examiner* — Susan McCormick Ewoldt
(74) *Attorney, Agent, or Firm* — Penny J. Aguirre

(57) ABSTRACT

A new cultivar of *Calendula* plant, '20123-29D', that is characterized by its compact plant habit with strong stems and thick leaves, its inflorescences with double ray florets that are bright yellow-orange in color, its long flowering time; blooming for 9 months from spring into winter in Noordwijkerhout, The Netherlands, its very high tolerance to powdery mildew, its very high tolerance to heat and cold, withstanding temperatures below −20° C. in the winter and its ability to be readily propagated by stem cuttings.

2 Drawing Sheets

Botanical classification: *Calendula officinalis.*
Variety denomination: '20123-29D'.

CROSS REFERENCE TO RELATED APPLICATIONS

This application is co-pending with U.S. Plant Patent Applications filed for plants derived from the same breeding program that are entitled *Calendula* Plant Named '20123-91D' (U.S. Plant patent application Ser. No. 14/121,628) and *Calendula* Plant Named '20124-30D' (U.S. Plant patent application Ser. No. 14/120,524).

BACKGROUND OF THE INVENTION

The present invention relates to a new and distinct cultivar of *Calendula* plant, botanically known as *Calendula officinalis* '20123-29D' and will be referred to hereinafter by its cultivar name, '20123-29D'. The new cultivar of *Calendula* is an herbaceous perennial grown for container and landscape use.

The new cultivar was derived from a controlled breeding program conducted by the Inventor in Katsuta-Gun, Okayama-Pref., Japan. The overall purpose of the breeding program was to develop new cultivars of vegetatively propagated *Calendula* plants with low-growing and well-spreading growth habits combined with long flowering periods and a unique range of flower colors.

The inventor made repeated crosses and selection of plants in his breeding program from 2008 through 2012 prior to selection of the new cultivar. '20123-29D' was selected in the Inventor's trial garden in 2012 as a single unique plant from amongst the seedlings derived from self-crossing an unnamed and unpatented plant from the Inventor's breeding program, ref. code 20122-24D, in 2012.

Asexual propagation of the new cultivar was first accomplished by softwood stem cuttings in summer of 2012 by the Inventor in Katsuta-Gun, Okayama-Pref., Japan. Asexual propagation by softwood stem cuttings has determined the characteristics of the new cultivar are stable and reproduced true to type in successive generations.

SUMMARY OF THE INVENTION

The following traits have been repeatedly observed and are determined to be the characteristics of the new cultivar. These attributes in combination distinguish '20123-29D' as a unique cultivar of *Calendula.*

1. '20123-29D' exhibits a compact plant habit with strong stems and thick leaves.
2. '20123-29D' exhibits inflorescences with double ray florets that are bright yellow-orange in color.
3. '20123-29D' exhibits a long flowering time; blooming for 9 months from spring into winter in Noordwijkerhout, The Netherlands.
4. '20123-29D' exhibits very high tolerance to powdery mildew caused by *Podosphaera xanthii.*
5. '20123-29D' exhibits very high tolerance to heat and cold, withstanding temperatures below −20° C. in the winter.
6. '20123-29D' is readily propagated by stem cuttings; *Calendula officinalis* is typically seed propagated.

'20123-29D' can best be compared to plants of the *Calendula* seed strain 'Alice'. 'Alice' differs from '20123-29D' in having flowers that are larger in size, in having a shorter four month long blooming period, in being poorly branched, in being susceptible to powdery mildew, heat, and cold, and in being propagated by seed. '20123-29D' can also be compared to the co-pending *Calendula* cultivars '20123-91D' and '20124-30D'. '20123-91D' differs from '20123-29D' in having inflorescences with double ray florets that are orange in color on the upper surface and orange and suffused with greyed-purple on the lower surface and in lacking disk florets. '20124-30D' differs from '20123-29D' in having inflorescences with ray florets that are more yellow in color. There are no cultivars of *Calendula officinalis* that are vegetatively propagated known to the Inventor. The Inventor has no records on the characteristics of the parent plant.

BRIEF DESCRIPTION OF THE DRAWINGS

The accompanying colored photographs illustrate the overall appearance and distinct characteristics of the new *Calendula*. The plant in the photograph is five months in age as grown outdoors in a 13-cm container in Noordwijkerhout, The Netherlands.

The photograph in FIG. 1 provides a side view of the plant habit of '20123-29D' in bloom.

Figure 1:
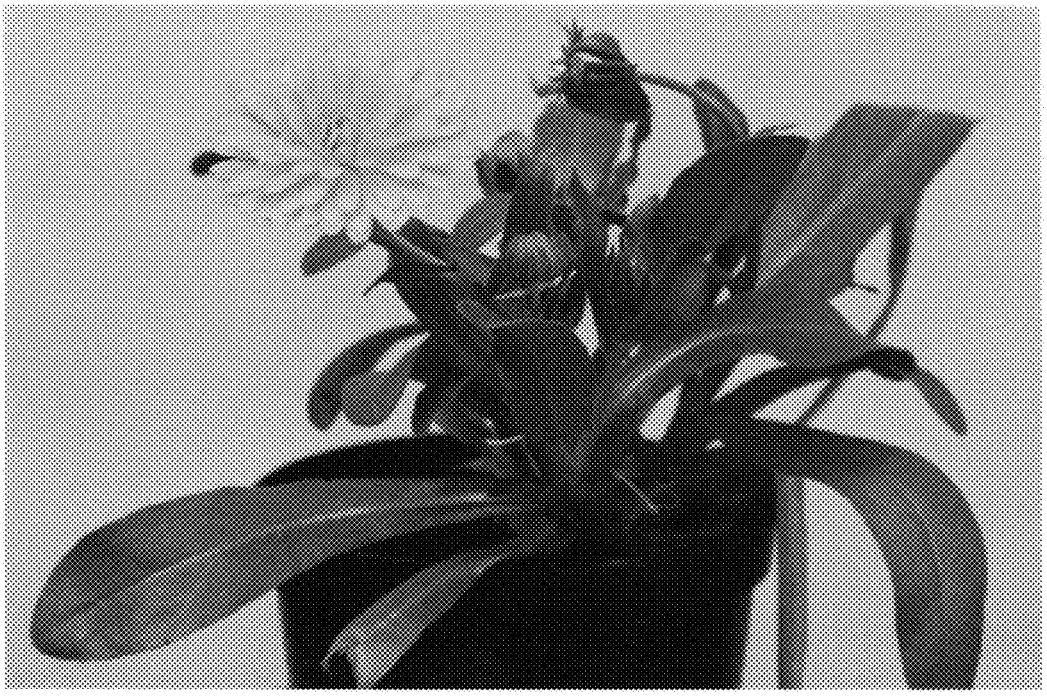
Figure 2:
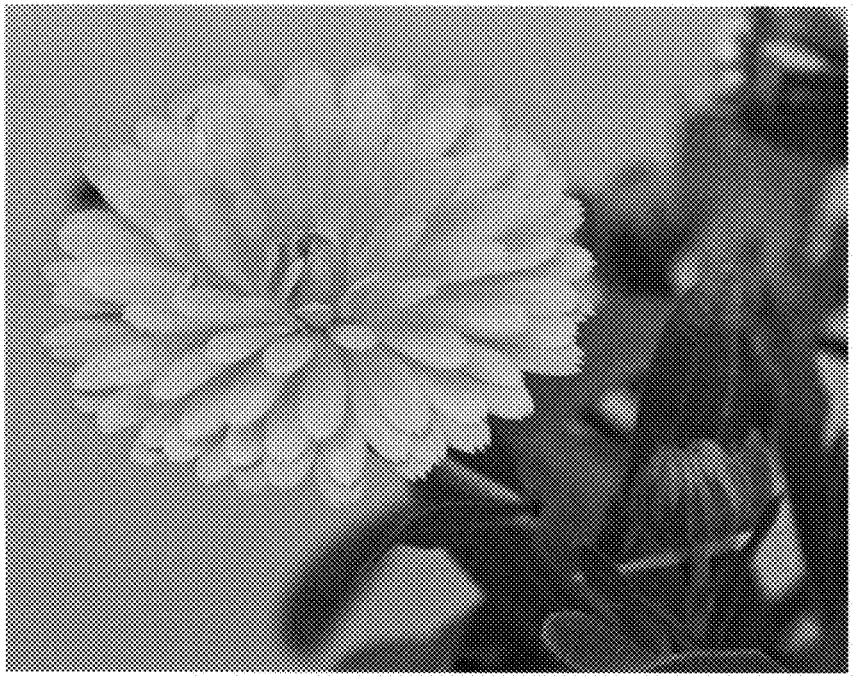

The photograph in FIG. 2 provides a close-up view of a mature inflorescence of '20123-29D'.

Figure 3:
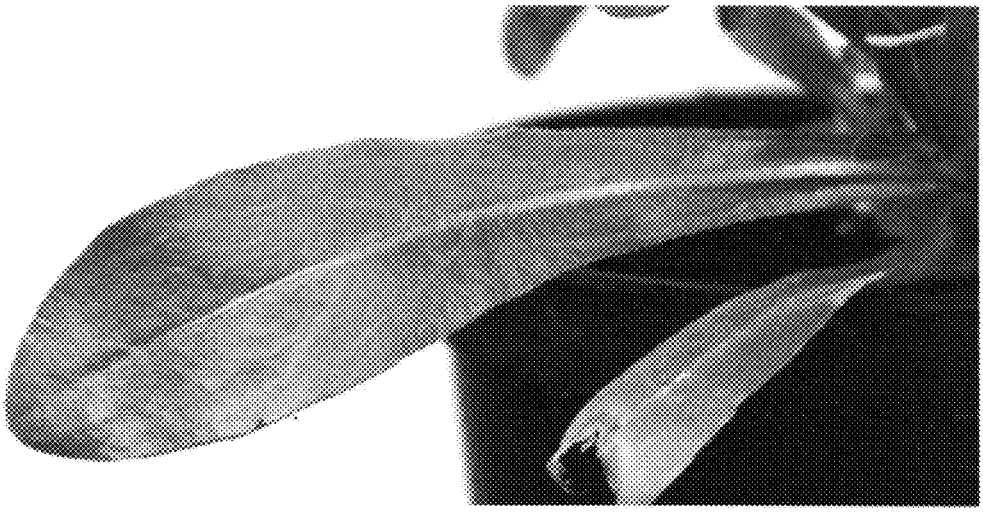

The photograph in FIG. 3 provides a close-up view of the foliage of '20123-29D'.

The colors in the photographs may differ slightly from the color values cited in the detailed botanical description, which accurately describe the colors of the new *Calendula*.

DETAILED BOTANICAL DESCRIPTION

The following is a detailed description of five month-old plants of the new cultivar as grown outdoors in 13-cm containers in Noordwijkerhout, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—An average of nine-months from spring into winter in Noordwijkerhout, The Netherlands.

*Plant type*.—Herbaceous perennial or grown as an annual in some climates.

*Plant habit*.—Compact with strong stems and thick leaves.

*Height and spread*.—Reaches an average of 13.9 cm in height and 26.3 cm in diameter.

*Cold hardiness*.—Observed to be hardy to U.S.D.A. Zone 7.

*Diseases*.—Observed to have very high tolerance to powdery mildew caused by *Podosphaera xanthii*.

*Root description*.—Fine and fibrous roots.

*Propagation*.—Stem cuttings.

*Vigor*.—Vigorous.

*Growth rate*.—An average of 10 cm a month in spring.

Stem description:

*Shape*.—Rounded.

*Stem color*.—143A.

*Stem size*.—An average of 10.7 cm in length and 4 mm in diameter.

*Stem strength*.—Strong.

*Stem aspect*.—Lateral stems grow in an angle of 35° to the main stem.

*Stem surface*.—Moderately glossy, sparsely covered with very short soft hairs; 1 mm in length and NN155D in color.

*Stem number*.—4 lateral branches.

*Internode length*.—Average of 2 cm in length.

*Branching*.—Branches grow from base.

Foliage description:

*Leaf shape*.—Narrow oblanceolate to narrow oblong.

*Leaf division*.—Simple.

*Leaf base*.—Truncate, decurrent.

*Leaf apex*.—Obtuse to broad acute, outer tip very short mucronulate.

*Leaf venation*.—Pinnate, color: upper surface; 144A, lower surface; 143A.

*Leaf margins*.—Entire, very sparsely covered with very short strigose hairs; average 0.4 mm in length and NN155D in color.

*Leaf attachment*.—Sessile.

*Leaf arrangement*.—Alternate.

*Leaf size*.—Average of 11.7 cm in length and 2.6 cm in width.

*Leaf color*.—Young upper surface; N137B, young lower surface; 137A, mature upper surface; 137A, mature lower surface; between 146B and 147B.

*Leaf surface*.—Upper surface is moderately glossy and slightly rough to the touch, very sparsely covered with very short strigose hairs average of 0.3 mm in length and NN155D in color, lower surface is very slightly glossy and slightly rough to the touch.

*Petioles*.—No petioles present, leaves are decurrent.

Inflorescence description:

*Inflorescence type*.—Terminal capitulum consisting of disc and ray florets.

*Inflorescence number*.—Average of 1 per lateral stem.

*Inflorescence fragrance*.—None.

*Inflorescence aspect*.—Straight on top of stem.

*Inflorescence longevity*.—A few weeks.

*Inflorescence size*.—Average of 2 cm in height and 6 cm in diameter.

*Inflorescence buds*.—Average of 2 per lateral stem, broad ovate to globular in shape, average of 1.1 cm in length and 1.2 cm in diameter, color; 138A to 138B, apex is 21A.

*Receptacle*.—No receptacle present.

*Peduncle*.—2.5 cm in length and 2 mm in diameter, terminal peduncle is straight on top of stem, moderate strength, moderately covered with short soft hairs; average of 1 mm in length and NN155D in color.

*Involucral bracts*.—Average of 28 per inflorescence, arranged in 2 rows, lanceolate in shape, narrowly acute apex, cuneate base, margin entire, 1 cm in length, 2 mm in width, upper surface is glabrous, lower surface is densely covered with very short pubescence; average length is 0.5 mm and NN155C in color, color; upper surface 137A to 137B, lower surface N137B.

Ray florets (pistillate):

*Number*.—Average of 110.

*Arrangement*.—Rotate, 5 whorls.

*Shape*.—Oblanceolate.

*Aspect*.—Slightly upright at the base, held in an average angle of 20°, whole ray floret near horizontal.

*Size*.—Average of 2.4 cm in length and 5 mm in width.

*Ray floret apex*.—Praemorse.

*Ray floret base*.—Narrow cuneate.

*Ray floret margins*.—Entire.

*Ray floret surface*.—Upper surface is matte, glabrous and velvety, lower surface is slightly glossy.

*Ray floret color*.—When opening upper surface; between 23A and 24A, base 9A, when opening lower surface; 21A, base 9A, when fully open upper surface; color between N25C and N25D, base 9A, when fully open lower surface; color between N25C and N25D, base 1B.

Disk florets (perfect): Glabrous and glossy surfaces, spirally placed on disc average of 10 disc florets per inflorescence, shape is tubular, upper $1/5^{th}$ of disk florets free, tip is acute, fused into tube, entire margin, average of 5 mm in length and 1.5 mm in width, color of upper and lower surfaces when opening and fully opened is 9C with mid-section 9C and base 150D.

Reproductive organs:

*Gynoecium*.—1 pistil per ray and disk floret, 5 mm in length, stigma unequal decurrent and 23A to 24A in color, style is 2 mm in length and 8C in color, ovary 150D in color.

*Androecium*.—5 stamens, filament length is 0.2 cm and 165B in color, anther is linear in shape, 2 mm in length and 155A in color, pollen amount is very low and too low to be measured by RHS-CC.

*Fruit and seed*.—No fruits or seeds have been observed to date.

It is claimed:

1. A new and distinct variety of *Calendula* plant named '20123-29D' as described and illustrated herein.

* * * * *